United States Patent
Shukla et al.

(10) Patent No.: US 6,537,502 B1
(45) Date of Patent: Mar. 25, 2003

(54) SURFACE COATED HOUSING FOR SAMPLE PREPARATION

(75) Inventors: Ashok K Shukla, Woodstock, MD (US); Amita M Shukla, Woodstock, MD (US); Mukta M Shukla, Woodstock, MD (US)

(73) Assignee: Harvard Apparatus, Inc., Holliston, MA (US)

( * ) Notice: Subject to any disclaimer, the term of this patent is extended or adjusted under 35 U.S.C. 154(b) by 195 days.

(21) Appl. No.: 09/625,559

(22) Filed: Jul. 25, 2000

(51) Int. Cl.[7] .............. B01L 3/02; G01N 1/00; B01D 15/08; B01D 24/00; B01D 39/00; C12Q 1/42

(52) U.S. Cl. ............ 422/101; 422/100; 436/174; 210/656; 210/500; 210/198.2; 435/21

(58) Field of Search ............... 422/100, 68.1, 422/70, 72, 73, 99, 101, 102; 73/863.23, 863.32, 864.01, 864.11, 864.71; 210/656, 500, 198.2; 435/21; 436/174, 180

(56) References Cited

U.S. PATENT DOCUMENTS

| | | | |
|---|---|---|---|
| 3,513,092 A | * 5/1970 | Matherine, Jr. | 210/198.3 |
| 4,384,958 A | 5/1983 | Wisebaker et al. | |
| 4,472,357 A | * 9/1984 | Levy et al. | |
| 4,793,920 A | * 12/1988 | Cortes et al. | 210/198.2 |
| 5,073,341 A | * 12/1991 | Hargreaves | |
| 5,084,240 A | * 1/1992 | Babson | |
| 5,098,845 A | * 3/1992 | Babson | |
| 5,234,667 A | * 8/1993 | Radtke et al. | |
| 5,236,604 A | * 8/1993 | Fiehler | |
| 5,244,635 A | * 9/1993 | Rabson et al. | |
| 5,318,748 A | * 6/1994 | Babson et al. | |
| 5,324,629 A | * 6/1994 | Phi-Wilson et al. | |
| 5,344,611 A | * 9/1994 | Volger et al. | |
| 5,346,672 A | * 9/1994 | Stapleton et al. | |
| 5,453,163 A | * 9/1995 | Yan | 204/451 |
| 5,552,325 A | * 9/1996 | Nochumson et al. | |

(List continued on next page.)

FOREIGN PATENT DOCUMENTS

| | | | | |
|---|---|---|---|---|
| EP | 0 197 729 | | 10/1986 | |
| FR | 2498331 A | * | 7/1982 | G01N/31/22 |
| WO | WO 98/37949 | | 9/1998 | |
| WO | WO 0107162 A1 | * | 2/2001 | |

OTHER PUBLICATIONS

WO 01/07162 A1 Shukla, et al. Suface Coated Housing for Sample Preparation Feb. 01, 2001.*
Aldrich Catalog (1994) p. T132, 1008–1009, Gas Chromatography Capillary columns.*
Harris, Daniel, Quantitative Chemical Analysis, 4th Ed. W.H. Freeman and Company, NY (1995) Chapter 23–1, pp. 656–670.*
Peters, Thomas L. "A Syringe Mountable Micro Adsorbent Column for the Concentration of Organics." Jul. 1, 1997. "Research Disclosure, GB, Industrial Opportunities Ltd." Havant, No. 399, p. 453. Whole document.

*Primary Examiner*—Jill Warden
*Assistant Examiner*—Brian R Gordon
(74) *Attorney, Agent, or Firm*—Hale and Dorr LLP

(57) ABSTRACT

This invention relates to a novel method for small sample preparation using a tube or column, such as a pipette tip, in which the interior surface is coated with a solid matrix for sample preparation. Said solid matrix is composed of a polymeric substance such as polytetrafluoroethylene (PTFE) and one or more column materials such as reactive or absorptive materials suited for sample filtration, separation or purification. The desired sample, containing biomolecules such as DNA, proteins or other molecular components, is passed through said tube or column, which may be a pipette tip, or like structure.

32 Claims, 2 Drawing Sheets

U.S. PATENT DOCUMENTS

| | | | |
|---|---|---|---|
| 5,660,797 A | * 8/1997 | Jarvimaki | 422/100 |
| 5,719,322 A | * 2/1998 | Lansbarkis et al. | 210/198.2 |
| 5,738,308 A | * 4/1998 | Leendersen | 428/422 |
| 5,783,308 A | * 7/1998 | Leendersen | 428/422 |
| 5,811,665 A | * 9/1998 | Gregor et al. | |
| 5,853,864 A | * 12/1998 | Brown | |
| 5,906,744 A | * 5/1999 | Carroll et al. | |
| 5,925,732 A | * 7/1999 | Ecker et al. | |
| 5,939,614 A | * 8/1999 | Walters et al. | 422/88 |
| 5,955,032 A | * 9/1999 | Kelly et al. | |
| 5,997,746 A | * 12/1999 | Valaskovic | 210/198.2 |
| 6,048,457 A | 4/2000 | Kopaciewicz | |
| 6,048,495 A | * 4/2000 | Marcoll | |
| 6,117,394 A | 9/2000 | Smith | |
| 6,143,250 A | * 11/2000 | Tajima | |
| 6,143,252 A | 11/2000 | Haxo, Jr. et al. | |
| 6,190,559 B1 | * 2/2001 | Valaskovic | 210/198.2 |
| 6,200,474 B1 | * 3/2001 | Kopaciewicz et al. | 210/321.6 |
| 6,274,726 B1 | * 8/2001 | Laugharn et al. | |
| 6,284,459 B1 | * 9/2001 | Nova et al. | |
| 6,301,952 B1 | * 10/2001 | De Zeeuw et al. | 210/656 |
| 6,416,716 B1 | * 7/2002 | Shukla et al. | 210/198.2 |

* cited by examiner

SURFACE COATED HOUSING FOR SAMPLE PREPARATION

FIELD OF THE INVENTION

This invention relates to a novel method for small sample preparation using a tube or column, such as a pipette tip, in which the interior surface is coated with a solid matrix for sample preparation. Said solid matrix is composed of a polymeric substance such as polytetrafluoroethylene (PTFE) and one or more column materials such as reactive or absorptive materials suited for sample filtration, separation or purification. The desired sample, containing bio-molecules such as DNA, proteins or other molecular components, is passed through said tube or column, which may be a pipette tip, or like structure.

Depending on the specifications of the column materials in the solid matrix, selected molecules from the sample can be separated or purified by binding to, or by being entrapped in, the column material components of the solid matrix. The bound molecules can later be eluted from the solid matrix by the use of different solvents. The tube described in the present invention has an opening at the top end, through which the sample is introduced into the tube and an open end at the bottom, through which selected components of the sample flow through during the sample separation process. Said tube may be of any shape or size in any configuration suitable for a given set of experimental conditions. The present invention is suited for samples with volumes from nanoliters to milliliters.

BACKGROUND OF THE INVENTION

Although a spectrum of analytical methods for small sample separation and purification have been developed, a number of problems, such as the slow speed of the separation process and the loss of sample volumes, limit the quality of currently available methods. The present invention describes a small sample preparation method that both speeds up the sample purification and separation process and minimizes the extent of sample loss. This invention is a method for sample preparation that uses a tube or column where the interior surface of said tube or column is coated with a solid matrix. The solid matrix contains a polymeric substance such as polytetrafluoroethylene (PTFE), as well as, column materials such as reactive or absorptive materials suited for sample filtration, size-based separation or purification. The column material can be composed of chromatographic media such as gel-filtration, ion-exchange, reverse-phase, and silica or modified silica media.

As mentioned above, currently available methods for the separation and purification of micro volumes of samples often result in undesirable sample loss. Since the volumes of desired molecules, such as proteins or bio-molecules, are often very small, the loss of even small volumes in such samples can represent a significant portion of the total sample. In currently available methods, sample loss often results due to the presence of filters or other components in the separation column. For example, currently available methods that use a filter or chromatographic material plug at the bottom of a pipette tip often result in the loss of sample on the filter or in the matrix containing the chromatography material. Since the volume of such a filter or plug may sometimes be as large as the volume of the micro sample itself, sample loss can be quite significant and is often accompanied by a slowed rate of separation. Also, different solvents interact differently with the filter itself further adding variation to the quality of the separation or purification of a particular sample.

One method that is currently available is the ZipTip developed by Millipore. This system consists of a micropipette tip that contains a cast of the column material in a porous matrix that is formed as a plug at the lower open end of the tip. Since the casted material plugs the open end through which the sample is pulled into the tip, however, the flow of the sample through the plug and into the tip may be slowed down or impeded by the plug. Furthermore, when this system is used in a multi-sample configuration such as a 96-well plate, there may be inconsistency in the quantity of sample that is absorbed into the different tips on the same plate and in the quality of the sample separation process itself.

In the invention described herein, the solid matrix is applied to the tube or pipette tip such that it coats the interior sides of the tube without significantly obstructing the flow of the sample through the lower opening of the tip. The solid matrix may be affixed to the interior walls of the tube using any physical or chemical methods that include, but are not limited to adhesion, heat, pressure and etching. For optimal sample separation, the sample can be aspirated back and forth multiple times to ensure optimal binding of the desired bio-molecules to the column material in the solid matrix. The bio-molecules can then be eluted from the solid matrix using different solvents.

The solid matrix coating is composed of one or more inert materials such as PTFE (polytetrafluoroethylene) and the desired column materials. Said desired column materials adhere to the inner surface of the tube when used in combination with said inert materials resulting in a solid matrix that is effective for sample separation. Sample separation and purification tubes designed with such an interior coat of the solid matrix are highly effective because the sample can flow more easily through the tube, column or pipette tip chamber and it is in contact with a greater surface area of the coated solid matrix containing the column material. The quality of sample preparation is also enhanced due to increased consistency in performing the same procedure whether in a single or simultaneous, multi-tip framework.

The various features of novelty, which characterize the invention, are pointed out with particularity in the claims annexed to and forming a part of this disclosure. For a better understanding of the invention, its advantages and objects, reference is made to the accompanying drawings and descriptive matter in which a preferred embodiment of the invention is illustrated.

BRIEF DESCRIPTION OF THE DRAWINGS

The foregoing and still other objects of this invention will become apparent, along with various advantages and features of novelty residing in the present embodiments, from study of the following drawings, in which.

DESCRIPTION OF THE PREFERRED EMBODIMENTS

Figure 1:
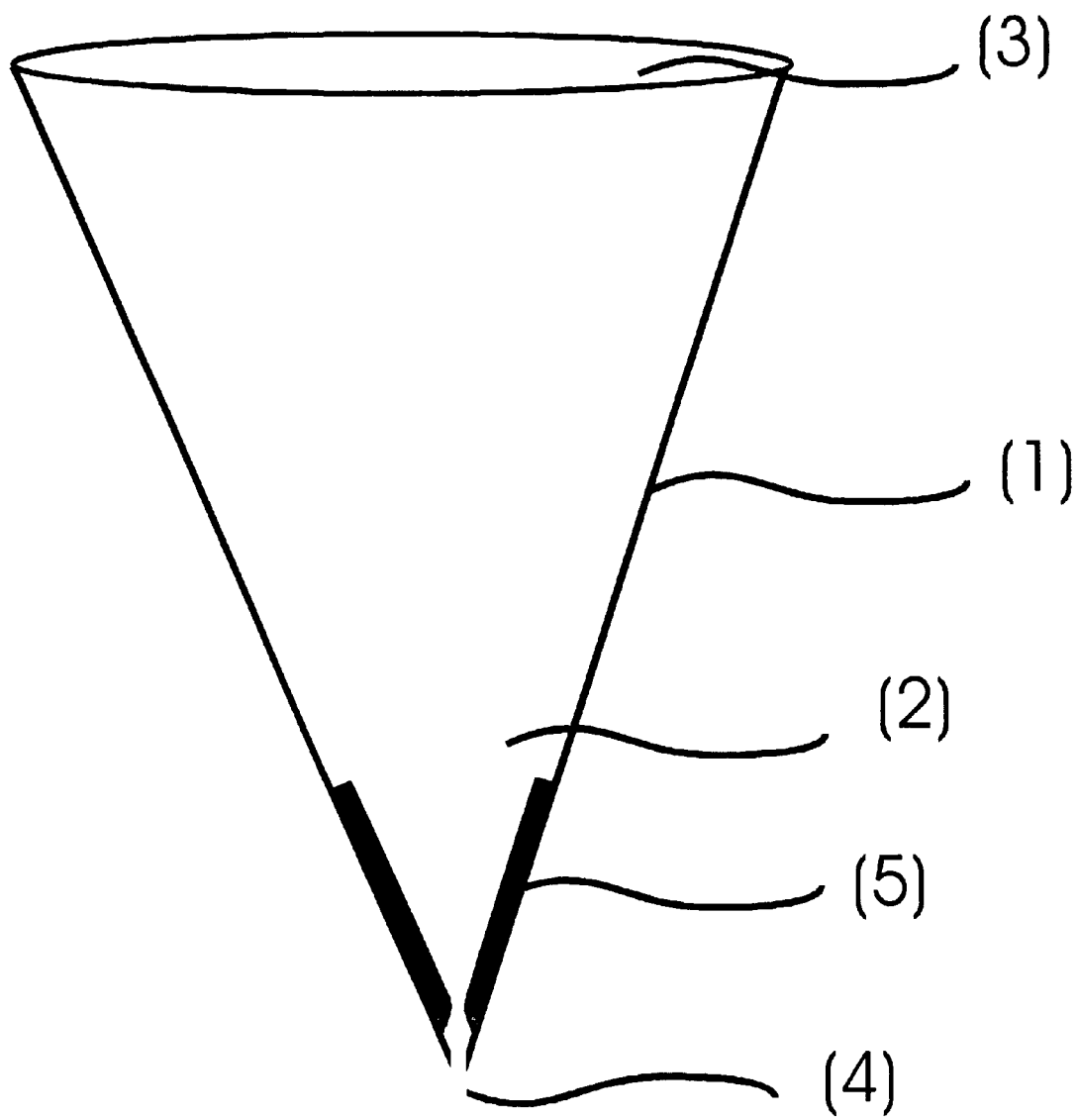
FIG. 1 is an expanded view of a tube, a pipette tip, coated on the interior with a solid matrix, according to the present invention.
Figure 2:
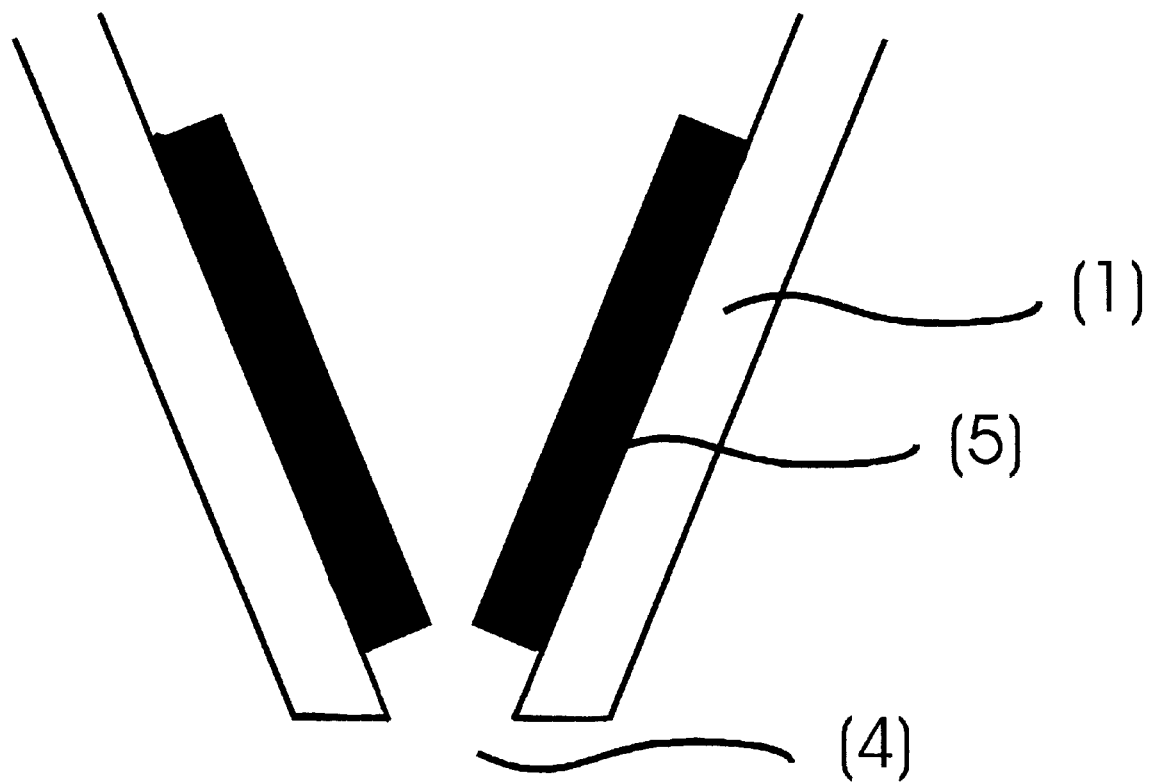
FIG. 2 is an expanded view of the lower opening of a tube, a pipette tip, coated on the interior with a solid matrix, according to the present invention.

Referring to the drawings, FIG. 1 shows a tube (1), in this instance a pipette tip that has a bottom end (2) and a top end (3) and an opening (4) in said bottom end. The tube (1) is coated on its interior sides with the solid matrix (5), as shown toward the bottom end of the tube in FIG. 1. The solid matrix (5) is composed of both an inert material and a chromatographic material. Said inert material particles, which may consist of a combination of one or more different inert materials, aggregate and during aggregation the chromatographic material particles are entrapped/embedded within them resulting in the solid matrix.

The tube, shown in FIG. 1 as a pipette tip, can be made of any material and in any configuration depending on the specifications of a given experiment. Said tube (1) may enclose a volume from 0.0001 to 100 milliliters. Said tube can be of any shape or size and can be composed of combination of one or more different polymer materials from the group consisting of, but not limited to, polytetrafluoroethylene, polysulfone, polyethersulfone, cellulose acetate, polystyrene, polystyrene/acrylonitrile copolymer and PVDF. One or both ends of said tube may be tapered and said tube can consist of a configuration where the inner diameter of said bottom end (2) is less than the inner diameter of said top end (3). The coating (5) may be located anywhere on the interior surface of said tube (5).

The chromatographic material can be silica, non-silica, polymer-based, active charcoal, zirconium, titanium or other materials. The solid matrix, which can be in powder form or woven or non-woven sheet form, can consist of one or more chromatographic materials (such as a mix of cation and anion exchange materials). The column material can also consist of other chromatographic media, gels, bacteria, living cells or solid powder.

The chromatographic material particles can be chemically or physically modified and may be porous or non-porous. The sizes of the inert or chromatographic material particles can be from nanometers to micrometers.

The tube can be in a singular format or part of a multiple-tube format such as 8, 12, 96, 384 or 1536—well micropipette plates. For example, 96 tips coated with the solid matrix in the interior can be used for the simultaneous preparation of up to 96 samples. Such multi-tip configurations can be designed with different numbers of tips forming the multi-tip system.

The tube (1) can have a cap or other mechanism to close one or both ends of the holding. Such a cap or similar device may or may not be attached to holding.

The broader usefulness of the invention may be illustrated by the following examples.

EXAMPLE 1

Purification of Cytochrome C

In This experiment, we used a 10–200 microliter pipette tip that was coated with T-30 (Teflon dispersion from Dupont) containing 150 mg C-4 silica powder. 50 microliters of solution was pulled in the pipette tip and ejected. The solution remaining on the pipette-tip walls was air dried and washed several times with distilled water and isopropanol solution. After drying, the tip was used to purify a sample containing cytochrom-C and Tris/SDS buffer. The cytochrom-c solution was pulled at-least 10–20 times into the pipette-tip and then the pipette-tip was washed with water to remove the salt and SDS. The cytochrom-C which was bound to the coating on the tip was eluted with 70% isopropanol and water. The eluted solution was analyzed by HPLC.

EXAMPLE 2

Purification of Albumin

This experiment is similar to Example 1. In place of cytochrom-C, bovine albumine was used and analyzed by HPLC.

While a specific embodiment of the invention has been shown and described in detail to illustrate the application of the principles of the invention, it is understood that the invention may be embodied otherwise without departing from such principles and that various modifications, alternate constructions, and equivalents will occur to those skilled in the area given the benefit of this disclosure and the embodiment described herein, as defined by the appended claims.

What is claimed is:

1. A pipette tip comprising an open top end, an open bottom end, and a solid matrix coating on the interior surface of the pipette tip, wherein the solid matrix coating comprises at least one chromatographic material and at least one inert material, and wherein the solid matrix coats the interior surface of the pipette tip without significantly obstructing the flow of the sample.

2. The pipette tip of claim 1, wherein the inert material is a polymer.

3. The pipette tip of claim 2, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

4. The pipette tip of claim 1, wherein the chromatographic material is a gel-filtration material, an ion-exchange material, a reverse-phase material, a silica, or a mixture of two or more thereof.

5. The pipette tip of claim 1, wherein the chromatographic material is a silica, a modified silica, a polymer, active charcoal, zirconium, titanium, or a mixture of two or more thereof.

6. The pipette tip of claim 1, wherein the pipette tip is a made of a polymer.

7. The pipette tip of claim 6, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

8. The pipette tip of claim 1, wherein the volume of the pipette tip is between 0.0001 ml and 100 ml.

9. The pipette tip of claim 1, further comprising a piston adjacent the top end of the pipette tip.

10. A pipette tip array comprising 8 pipette tips of claim 1.

11. A pipette tip array comprising 12 pipette tips of claim 1.

12. A pipette tip array comprising 96 pipette tips of claim 1.

13. A pipette tip array comprising 384 pipette tips of claim 1.

14. A pipette tip array comprising 1,536 pipette tips of claim 1.

15. A container comprising an open top end, a closed bottom end, and a solid matrix coating on the interior surface of the container, wherein the solid matrix coating comprises at least one chromatographic material and at least one inert material, and wherein the solid matrix coats the interior surface of the container without significantly obstructing the flow of the sample.

16. A container array comprising 8, 12, 96, 384 or 1536 containers of claim 15.

17. The container of claim 15, wherein the inert material is a polymer.

18. The container of claim 17, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

19. The container of claim 15, wherein the chromatographic material is a gel-filtration material, an ion-exchange material, a reverse-phase material, a silica, or a mixture of two or more thereof.

20. The container of claim 15, wherein the chromatographic material is a silica, a modified silica, a polymer, active charcoal, zirconium, titanium, or a mixture of two or more thereof.

21. The container of claim 15, wherein the container is a made of a polymer.

22. The container of claim 21, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

23. The container of claim 15, wherein the volume of the container is between 0.0001 ml and 100 ml.

24. A tube comprising an open top end, an open bottom end, and a solid matrix coating on the interior surface of the tube, wherein the solid matrix coating comprises at least one chromatographic material and at least one inert material, and wherein the solid matrix coats the interior surface of the tube without significantly obstructing the flow of the sample.

25. A tube array comprising 8, 12, 96, 384 or 1536 tubes of claim 24.

26. The tube of claim 24, wherein the inert material is a polymer.

27. The tube of claim 26, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

28. The tube of claim 24, wherein the chromatographic material is a gel-filtration material, an ion-exchange material, a reverse-phase material, a silica, or a mixture of two or more thereof.

29. The tube of claim 24, wherein the chromatographic material is a silica, a modified silica, a polymer, active charcoal, zirconium, titanium, or a mixture of two or more thereof.

30. The tube of claim 24, wherein the tube is a made of a polymer.

31. The tube of claim 29, wherein the polymer is a polytetrafluoroethylene, a polysulfone, a polyethersulfone, a cellulose acetate, a polystyrene, a polystyrene/acrylonitrile copolymer, a polyvinylidene fluoride, or a mixture of two or more thereof.

32. The tube of claim 24, wherein the volume of the tube is between 0.0001 ml and 100 ml.

* * * * *